United States Patent [19]

Hagen et al.

[11] Patent Number: 4,767,612

[45] Date of Patent: Aug. 30, 1988

[54] TRIAMCINOLONE ACETONIDE FOR THE TREATMENT OF ALLERGIC RHINITIS

[75] Inventors: Nicholas S. Hagen, Doylestown; Kim D. Lamon, Maple Glen, both of Pa.

[73] Assignee: Rorer Pharmaceutical Corporation, Fort Washington, Pa.

[21] Appl. No.: 6,397

[22] Filed: Jan. 23, 1987

[51] Int. Cl.⁴ .................. A61K 9/12; A61K 31/01; A61K 47/00
[52] U.S. Cl. ..................................... 424/45; 424/46; 424/434; 514/850; 514/853
[58] Field of Search ..................... 424/45, 46, 434; 514/850, 853

[56] References Cited

U.S. PATENT DOCUMENTS 4,294,829 10/1981 Suzuki et al. .................. 514/174
4,419,352 12/1983 Cox et al. ...................... 514/228

Primary Examiner—John Kight
Assistant Examiner—S. A. Acquah

[57] ABSTRACT

Disclosed is a method for the treatment of allergic rhinitis that manifests itself as rhinorrhea, nasal itching, sneezing, congestion and postnasal drip. The method comprises the administration from a nasal aerosol dispenser an effective amount of micronized triamcinolone acetonide suspended in dichlorodifluoromethane into the nasal cavity of a patient suffering from allergic rhinitis.

2 Claims, No Drawings

TRIAMCINOLONE ACETONIDE FOR THE TREATMENT OF ALLERGIC RHINITIS

BACKGROUND OF THE INVENTION

1. Field of the Invention

This invention relates to the treatment of allergic rhinitis with an aerosol formulation containing the active ingredient triamcinolone acetonide.

Allergic rhinitis denotes the allergic reactions of the nasal mucosa having the symptoms of rhinorrhea, nasal itching, sneezing, congestion and postnasal drip. Allergic rhinitis may occur seasonally, such as hay fever, or continuously throughout the year. It is caused by an allergen to which the individual is exposed, such as dust, danders, food, mold and the like, and is characterized by sudden attacks of sneezing, swelling of the nasal mucosa with watery discharge, itching of the eyes and lacrimation. These symptoms are treated usually with antihistamines, decongestants, immunotherapy or other rhinitis medications with varying degrees of success. However, such treatments are not entirely satisfactory.

2. Description of the Prior Art

Triamcinolone acetonide is an 11-beta-hydroxy glucocorticoid having the chemical name of 9α-fluoro-11β, 21-dihydroxy-16,17α-isopropyl-idene-dioxy-1,4-pregnadiene-3,20-dione and the structural formula of:

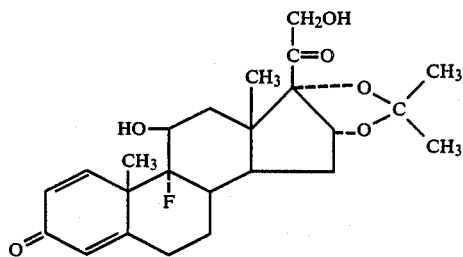

It is well known in the art, its process of synthesis has been disclosed in U.S. Pat. Nos. 2,990,401 and 3,035,050, as well as its use in various compositions directed to the treatment of divers ailments, conditions and symptoms of conditions. Examples of such compositions and use for treatment are as follows.

U.S. Pat. No. 3,312,594 issued on Apr. 4, 1967 to Cyr et al. discloses long-lasting troches and pastilles for the treatment of conditions in the oral cavity. Triamcinolone acetonide is one of the active ingredients used in the troches and pastilles for the treatment of inflammatory conditions.

U.S. Pat. No. 3,352,753 issued on Nov. 14, 1967 to L. J. Lerner teaches a topical gelled composition containing triamcinolone acetonide for treating dermatitis, insect bites, and infantile eczema.

U.S. Pat. No. 3,867,528 issued on Feb. 18, 1975 to Ritter et al. relates to a topical cream base which provides rapid and thorough penetration of the skin by steroids contained therein. The steroids disclosed include triamcinolone acetonide.

U.S. Pat. No. 3,897,779 issued on Aug. 5, 1975 to L. F. Hansen discloses a method of treating asthma with a suspension of finely divided triamcinolone acetonide in a chlorofluoroalkane.

U.S. Pat. No. 4,083,974 issued to J. S. Turi on Apr. 11, 1978 pertains to anti-inflammatory compositions in ointment form, containing steroids which include triamcinolone acetonide.

U.S. Pat. No. 4,466,956 issued to R. Leeds on Aug. 21, 1984 teaches a method of therapy for oral herpes simplex which comprises the application to the affected area of povidone-iodide followed by the application of diluted triamcinolone acetonide.

In parallel with the patent literature, products containing triamcinolone acetonide for the treatment of various ailments, conditions and symptoms of conditions are available on the market in various forms, such as, creams, ointments, sprays, injections and inhalants.

To our knowledge there is no product, disclosure, or suggestion whatsoever as to the treatment of allergic rhinitis with an aerosol formulation containing the active ingredient triamcinolone acetonide.

SUMMARY OF INVENTION

In accordance with the present invention, there is provided a method for the treatment of allergic rhinitis which comprises: the administration of an effective amount of micronized triamcinolone acetonide suspended in dichlorodifluoromethane into the nasal cavity of a patient suffering from such condition utilizing a nasal aerosol dispenser.

Clinical studies conducted, utilizing formulations of the present invention, evidenced efficacy in controlling the nasal allergy symptoms of nasal discharge, stuffiness and sneezing.

DETAILED DESCRIPTION OF THE INVENTION

The Aerosol Dispenser

The formulations of the present invention are contained in an aerosol dispenser or can. Such containers are well known in the art and can be made of stainless steel, aluminum, glass, plastic or plastic covered glass and are equipped with a valve or actuator for the dispensing of the pressurized content contained therein. Such aerosol dispensers are described, for example, in U.S. Pat. Nos. 2,992,645; 3,012,555; 3,219,533 and 3,897,779.

The Formulations

The commercially available triamcinolone acetonide is finely divided to a particle size of about 0.5 to 10, and preferably of about 1 to 5 microns in diameter and suspended in a pharmaceutically acceptable propellant such as a chlorofluoroalkane and preferably dichlorodifluoromethane (P-12). For ease of dispersion a dispersing agent, such as anhydrous ethanol, or sorbitan trioleate is used. The components are mixed, and pressure filled into aerosol dispensers.

Example 1 illustrates the process of making formulations of the present invention.

EXAMPLE 1

Triamcinolone acetonide was micronized in a fluid energy mill until 90–95% by weight was in the particle size range of 1 to 5 microns. Into a beaker was added 33.75 g of the micronized triamcinolone acetonide, followed by the addition of 104.46 g of anhydrous ethanol. Using a mechanical stirrer (homogenizer) the content of the beaker was thoroughly mixed and a homogeneous suspension obtained.

23 mg of the homogeneous slurry was metered into each of several aerosol cans. The cans were then crimped with a pressure valve, such as a Valois valve, and each charged with 15.0 g of P-12.

It is to be noted that various strengths of products can be made by using the homogeneous slurry of triamcinolone acetonide and anhydrous ethanol by varying the amount of slurry added to each aerosol can.

Other methods of preparation known in the prior art can also be used.

Formulations contained in aerosol cans were made to contain the following amounts of components:

| Dose mcg/Spray | Triamcinolone Acetonide (mg) | Ethanol 200 Proof (mg) | P-12 (g) |
|---|---|---|---|
| 10 | 2.8 (0.0188)* | 8.7 (0.0584)* | 14.89 (99.92)* |
| 25 | 5.6 (0.0376) | 17.4 (0.117) | 14.87 (99.85) |
| 50 | 11.2 (0.0753) | 34.8 (0.234) | 14.82 (99.69) |
| 100 | 22.5 (0.152) | 69.5 (0.468) | 14.75 (99.38) |
| 200 | 44.9 (0.304) | 139.1 (0.942) | 14.59 (98.75) |
| 500 | 112.3 (0.770) | 347.7 (2.38) | 14.12 (96.84) |

*Values in parentheses are percent by weight

Testing of the Formulations

The effects of triamcinolone acetonide (hereinafter TA) in nasal aerosol form, according to the invention, was studied in clinical trials. The objectives of the study were to evaluate the safety and efficacy of increasing doses of TA in patients with allergic rhinitis. A total of 111 patients with allergic rhinitis were enrolled in a double-blind, placebo controlled, parallel group study. The diagnosis of allergic rhinitis was established by a positive response to a skin test using appropriate pollen and mold spore allergens to confirm the clinical history of the disease. On the average, the patients had a long history of rhinitis (mean: 20 years) which was inadequately controlled by antihistamines.

The formulations used for the clinical study were as follows:

STUDY MEDICATION FORMULATIONS

| Components | | | | | |
|---|---|---|---|---|---|
| Triamcinolone Acetonide, USP | 0 mg | 3.75 mg | 7.5 mg | 15.0 mg | 30.0 mg |
| Alcohol, USP-200 Proof | 120 mg | 123.75 mg | 120.0 mg | 112.5 mg | 97.5 mg |
| Dichlorodifuloromethane, NF (P-12) | 9.75 mg | 9.75 mg | 9.75 mg | 9.75 mg | 9.75 mg |
| Sorbitan Trioleate (Span 85) | 0–10 mg | 0–10 mg | 0–10 mg | 0–10 mg | 0–10 mg |

The parallel group treatments were as follows:

| | Dosage Groups | Total Daily Dose |
|---|---|---|
| Placebo | 0 mcg, (4 × a day) | — |
| TA | 25 mcg, (4 × a day) | 200 mcg |
| TA | 50 mcg, (4 × a day) | 400 mcg |
| TA | 100 mcg, (4 × a day) | 800 mcg |
| TA | 200 mcg, (4 × a day) | 1,600 mcg |

The formulation was administered as a single spray in each nostril from an aerosol dispenser.

Efficacy was established by means of three independent parameters:

(a) intensity ratings of allergy symptoms, namely, nasal discharge, nasal stuffiness, sneezing, tearing and itchiness of the eyes;

(b) physicians' global impressions of the treatment; and (c) patients' global impressions of the treatment.

Results are shown in the Tables that follow:

Table I shows mean changes from baseline in intensity ratings of allergy symptoms;

Table II shows physicians' global evaluations; and

Table III shows patients' global evaluations.

TABLE I

NASAL ALLERGY SYMPTOM VARIABLES: MEAN CHANGES FROM BASELINE

| Evaluation Period | TA (mcg/ actuation) | N | Nasal Index[c] | Rhinitis Symptoms[d] | | |
|---|---|---|---|---|---|---|
| | | | | Sneezing | Nasal Discharge | Nasal Stuffiness |
| Baseline | 0 | 21 | 2.2 | 1.5 | 2.3 | 2.6 |
| | 25 | 21 | 2.2 | 2.0 | 2.3 | 2.4 |
| | 50 | 21 | 2.1 | 1.7 | 2.3 | 2.4 |
| | 100 | 22 | 2.3 | 1.9 | 2.3 | 2.7 |
| | 200 | 21 | 2.2 | 2.2 | 2.0 | 2.5 |
| Week 1 | 0 | 21 | −0.37 | −0.33 | −0.43 | −0.42 |
| | 25 | 21 | −0.83[a] | −0.80[a] | −0.95[a] | −0.69 |
| | 50 | 21 | −0.81[a] | −0.87[a] | −0.81 | −0.77 |
| | 100 | 22 | −0.84[a] | −0.88[a] | −0.74 | −0.90[a] |
| | 200 | 21 | −0.92[a] | −0.92[a] | −0.97[a] | −0.82[b] |
| Week 2 | 0 | 21 | −0.81 | −0.70 | −0.81 | −0.98 |
| | 25 | 20 | −1.29[a] | −1.45[a] | −1.38[a] | −1.00 |
| | 50 | 20 | −1.10 | −1.17[a] | −1.00 | −1.13 |
| | 100 | 20 | −1.15[b] | −1.26[a] | −1.05 | −1.17 |
| | 200 | 21 | −1.28[a] | −1.28[a] | −1.28[a] | −1.25 |
| LOBF | 0 | 21 | −1.06 | −0.94 | −1.15 | −1.13 |
| | 25 | 21 | −1.52[a] | −1.49[a] | −1.67[a] | −1.35 |
| | 50 | 21 | −1.16 | −1.16 | −1.13 | −1.15 |
| | 100 | 22 | −1.25 | −1.20 | −1.16 | −1.41 |
| | 200 | 21 | −1.56[a] | −1.42[a] | −1.58[b] | −1.66[a] |
| Overall | 0 | 21 | −0.82 | −0.72 | −0.86 | −0.93 |
| | 25 | 21 | −1.21[a] | −1.23[a] | −1.32[a] | −1.04 |
| | 50 | 21 | −1.02 | −1.07[a] | −0.97 | −1.01 |
| | 100 | 22 | −1.11 | −1.14[a] | −1.01 | −1.20 |
| | 200 | 21 | −1.32[a] | −1.25[a] | −1.35[a] | −1.33[b] |

[a]Degree of change from baseline is statistically significantly different, TA vs. placebo, $p \leq 0.05$.
[b]Degree of change from the baseline is marginally statistically significantly different, TA vs. placebo, $0.10 \geq p > 0.05$.
[c]Nasal Index is the average of Sneezing, Nasal Discharge and Nasal Stuffiness.
[d]Rhinitis symptoms were rated on a four-point scale from 0 = absent, to 3 = severe.
[e]LOBF = patient's last week mean value.

TABLE II

PHYSICIANS' GLOBAL EVALUATIONS (PERCENTAGES OF PATIENTS)

| Treatment/Wk (mcg/actuation) | N | Improved | No Change | Worsened |
|---|---|---|---|---|
| 0 (Placebo) | | | | |
| 1 | 21 | 52.4 | 38.1 | 9.5 |
| 2 | 21 | 71.4 | 14.3 | 14.3 |
| 3 | 19 | 73.7 | 21.1 | 5.3 |
| 4 | 19 | 78.9 | 21.1 | 0 |
| LOBF | 21 | 71.4 | 19.0 | 9.5 |
| TA:25 | | | | |
| 1 | 21 | 81.0[b] | 19.0 | 0 |
| 2 | 20 | 80.0 | 20.0 | 0 |
| 3 | 19 | 89.5 | 5.3 | 5.3 |
| 4 | 18 | 83.3 | 16.7 | 0 |

TABLE II-continued

PHYSICIANS' GLOBAL EVALUATIONS
(PERCENTAGES OF PATIENTS)

| Treatment/Wk (mcg/actuation) | N | Improved | No Change | Worsened |
|---|---|---|---|---|
| LOBF | 21 | 76.2 | 23.8 | 0 |
| TA:50 | | | | |
| 1 | 21 | 71.4 | 19.0 | 9.6 |
| 2 | 20 | 85.0 | 15.0 | 0 |
| 3 | 17 | 76.5 | 23.5 | 0 |
| 4 | 17 | 88.2 | 11.8 | 0 |
| LOBF | 21 | 85.7 | 9.5 | 4.8 |
| TA:100 | | | | |
| 1 | 22 | 81.8[a] | 18.2 | 0 |
| 2 | 18 | 100.0[a] | 0 | 0 |
| 3 | 18 | 94.4 | 5.6 | 0 |
| 4 | 19 | 89.5 | 10.5 | 0 |
| LOBF | 22 | 86.4 | 13.6 | 0 |
| TA:200 | | | | |
| 1 | 21 | 85.7[a] | 9.5 | 4.8 |
| 2 | 20 | 95.0[b] | 5.0 | 0 |
| 3 | 21 | 95.2[b] | 4.8 | 0 |
| 4 | 20 | 95.0 | 5.0 | 0 |
| LOBF | 21 | 95.2 | 4.8 | 0 |

[a]Significantly different from placebo, $p \leq 0.05$, Fisher's exact test.
[b]Marginally significant different from placebo, $0.10 \geq p > 0.05$, Fisher's exact test.

TABLE III

PATIENTS' GLOBAL EVALUATIONS
(PERCENTAGES OF PATIENTS)

| Treatment/Wk (mcg/actuation) | N | Improved | No Change | Worsened |
|---|---|---|---|---|
| 0 (Placebo) | | | | |
| 1 | 21 | 57.1 | 23.8 | 19.0 |
| 2 | 21 | 76.2 | 9.5 | 14.3 |
| 3 | 19 | 78.9 | 15.8 | 5.3 |
| 4 | 19 | 78.9 | 21.1 | 0 |
| LOBF | 21 | 71.4 | 19.0 | 9.5 |
| TA:25 | | | | |
| 1 | 21 | 81.0 | 19.0 | 0 |
| 2 | 20 | 85.0 | 10.0 | 5.0 |
| 3 | 19 | 89.5 | 5.3 | 5.3 |
| 4 | 18 | 88.9 | 11.1 | 0 |
| LOBF | 21 | 81.0 | 19.0 | 0 |
| TA:50 | | | | |
| 1 | 21 | 71.4 | 19.0 | 9.6 |
| 2 | 20 | 85.0 | 10.0 | 5.0 |
| 3 | 17 | 88.2 | 11.8 | 0 |
| 4 | 17 | 88.2 | 11.8 | 0 |
| LOBF | 21 | 85.7 | 9.5 | 4.8 |
| TA:100 | | | | |
| 1 | 22 | 81.8[b] | 18.2 | 0 |
| 2 | 18 | 100.0[a] | 0 | 0 |
| 3 | 18 | 94.4 | 5.6 | 0 |
| 4 | 19 | 89.5 | 10.5 | 0 |
| LOBF | 22 | 86.4 | 13.6 | 0 |
| TA:200 | | | | |
| 1 | 21 | 90.5[a] | 4.8 | 4.8 |
| 2 | 20 | 100.0[a] | 0 | 0 |
| 3 | 21 | 95.2 | 4.8 | 0 |
| 4 | 20 | 95.0 | 5.0 | 0 |
| LOBF | 21 | 95.2 | 4.8 | 0 |

[a]Significantly different from placebo, $p \leq 0.05$, Fisher's exact test.
[b]Marginally significantly different from placebo, $0.10 \geq p > 0.05$, Fisher's exact test.

As can be clearly seen in Table I, the symptom intensity ratings shows that all doses of TA are better than the placebo in improving allergy symptoms. Allergy improvement was greatest in the symptoms of sneezing and nasal discharges.

The conclusion that TA was better than placebo was supported also by the physicians' and patients' assessments of the overall effectiveness of the treatment, as shown in Tables II and III. Specifically noted were the percentages of patients the physicians rated as improved and the percentages of patients who rated themselves as improved. In the global evaluations by both physicians and patients the difference between placebo and TA numerically favored treatments with 25 mcg TA/spray and 50 mcg TA/spray, but statistically significantly favored treatments with 100 mcg TA/spray and 200 mcg TA/spray.

As to safety and side effects, no clinically significant changes were observed, such as weight, vital signs and laboratory parameters, among patients in any of the five treatment groups.

In summary, the results indicate that triamcinolone acetonide nasal aerosol can be used successfully for the control and treatment of nasal allergy suymptoms. It appears that this objective can be accomplished with a daily dose of about 100 to 1,600 mcg, and preferably a daily dose of about 200 to 800 mcg of triamcinolone acetonide.

Having described the presently preferred embodiment of the invention, the advantages and objects of the invention will be apparent to those skilled in the art and reasonable modifications thereto are fully contemplated herein without departing from the true spirit of the invention. Accordingly, there are covered all alternatives, modifications, and equivalents as may be included within the spirit and scope of the invention as defined solely by the appended claims.

What is claimed is:

1. A method for the control and treatment of allergic rhinitis in a patient having the symptoms of rhinorrhea, nasal itching, sneezing, congestion and postnasal drip comprising the administration into the nasal cavity of said patient a nasal spray from an aerosol dispenser, said nasal spray consisting essentially of by weight:

3.75 to 30.0 mg of micronized triamcinolone acetonide;
   123.75 to 97.5 mg of anhydrous ethanol;
   9.75 gm of dichlorodifluoromethane; and
   0 to 10 mg of sorbitan trioleate.

2. A method for the control and treatment of allergic rhinitis according to claim 1 wherein the administration of said nasal spray into the nasal cavity of said patient comprises the delivery of a daily dose of 200 to 1,600 mcg of micronized triamcinolone acetonide.

* * * * *